United States Patent
Lee et al.

(10) Patent No.: US 10,851,142 B2
(45) Date of Patent: Dec. 1, 2020

(54) HETERODIMERIC VASCULAR ENDOTHELIAL GROWTH FACTOR AND USE THEREOF

(71) Applicant: National Health Research Institutes, Miaoli County (TW)

(72) Inventors: Alan Yueh-Luen Lee, Miaoli County (TW); Jui-Ling Tsai, Miaoli County (TW)

(73) Assignee: National Health Research Institutes, Zhunan (TW)

( * ) Notice: Subject to any disclaimer, the term of this patent is extended or adjusted under 35 U.S.C. 154(b) by 175 days.

(21) Appl. No.: 15/780,734

(22) PCT Filed: Dec. 2, 2016

(86) PCT No.: PCT/US2016/064554
§ 371 (c)(1),
(2) Date: Jun. 1, 2018

(87) PCT Pub. No.: WO2017/096124
PCT Pub. Date: Jun. 8, 2017

(65) Prior Publication Data
US 2018/0355004 A1  Dec. 13, 2018

Related U.S. Application Data

(60) Provisional application No. 62/262,630, filed on Dec. 3, 2015.

(51) Int. Cl.
*A61K 38/18* (2006.01)
*C07K 14/475* (2006.01)

(52) U.S. Cl.
CPC ........ *C07K 14/475* (2013.01); *A61K 38/1866* (2013.01); *C07K 2319/02* (2013.01); *C07K 2319/21* (2013.01); *C07K 2319/30* (2013.01)

(58) Field of Classification Search
None
See application file for complete search history.

(56) References Cited

U.S. PATENT DOCUMENTS 9,284,369 B2 * 3/2016 Ferrara .................... A61P 3/04
2003/0027751 A1 2/2003 Kovesdi et al.
2009/0252729 A1 10/2009 Farrington et al.

OTHER PUBLICATIONS

Czajkowsky et al "Fc-Fusion Proteins: New Developments and Future Perspectives" EMBO Molecular Medicine vol. 4, pp. 1015-1028, 2012.
Pechtner et al "A New Approach to Drug Therapy: Fc-Fusion Technology" Primary Health Care vol. 7, pp. 1-5, 2017.
Boesen et al "Single-Chain Vascular Endothelial Growth Factor Variant with Antagonist Activity" The Journal of Biological Chemistry vol. 277, pp. 40335-40341, 2002.
Siemeister et al "An Antagonistic Vascular Endothelial Growth Factor (VEGF) Variant Inhibits VEGF-Stimulated Receptor Autophosphorylation and Proliferation of Human Endothelial Cells" Proceedings of the National Academy of Sciences USA vol. 95, pp. 4625-4629, 1998.
Siemeister et al "The α-Helical Domain Near the Amino Terminus is Essential for Dimerization of Vascular Endothelial Growth Factor" The Journal of Biological Chemistry vol. 273, pp. 11115-11120, 1998.
Tsai et al "The Novel $VEGF_{121}$-$VEGF_{165}$ Fusion Attenuates Angiogenesis and Drug Resistance via Targeting VEGFR2-HIF-1α-$VEGF_{165}$/Lon Signaling Through PI3K-AKT-mTOR Pathway" Current Cancer Drug Targets vol. 16, 2016.

* cited by examiner

*Primary Examiner* — Christine J Saoud
(74) *Attorney, Agent, or Firm* — Cesari and McKenna, LLP

(57) ABSTRACT

A fusion protein, comprising: (i) a first vascular endothelial growth factor (VEGF) isoform, and (ii) a second VEGF isoform, and (iii) a dimerization domain between the first isoform and the second isoform, wherein the first isoform and the second isoform are selected from $VEGF_{121}$ and $VEGF_{165}$.

12 Claims, 7 Drawing Sheets

Specification includes a Sequence Listing.

A

B

A

B

A

B

SEQUENCE LISTING

```
<160> NUMBER OF SEQ ID NOS: 11

<210> SEQ ID NO 1
<211> LENGTH: 444
<212> TYPE: DNA
<213> ORGANISM: Homo sapiens
<220> FEATURE:
<221> NAME/KEY: CDS
<222> LOCATION: (1)..(444)
<223> OTHER INFORMATION: VEGF121

<400> SEQUENCE: 1 atg aac ttt ctg ctg tct tgg gtg cat tgg agc ctt gcc ttg ctg ctc      48
Met Asn Phe Leu Leu Ser Trp Val His Trp Ser Leu Ala Leu Leu Leu
1               5                   10                  15 tac ctc cac cat gcc aag tgg tcc cag gct gca ccc atg gca gaa gga      96
Tyr Leu His His Ala Lys Trp Ser Gln Ala Ala Pro Met Ala Glu Gly
            20                  25                  30 gga ggg cag aat cat cac gaa gtg gtg aag ttc atg gat gtc tat cag     144
Gly Gly Gln Asn His His Glu Val Val Lys Phe Met Asp Val Tyr Gln
        35                  40                  45
```

```
cgc agc tac tgc cat cca atc gag acc ctg gtg gac atc ttc cag gag      192
Arg Ser Tyr Cys His Pro Ile Glu Thr Leu Val Asp Ile Phe Gln Glu
    50                  55                  60 tac cct gat gag atc gag tac atc ttc aag cca tcc tgt gtg ccc ctg      240
Tyr Pro Asp Glu Ile Glu Tyr Ile Phe Lys Pro Ser Cys Val Pro Leu
 65                  70                  75                  80 atg cga tgc ggg ggc tgc tgc aat gac gag ggc ctg gag tgt gtg ccc      288
Met Arg Cys Gly Gly Cys Cys Asn Asp Glu Gly Leu Glu Cys Val Pro
                 85                  90                  95 act gag gag tcc aac atc acc atg cag att atg cgg atc aaa cct cac      336
Thr Glu Glu Ser Asn Ile Thr Met Gln Ile Met Arg Ile Lys Pro His
                100                 105                 110 caa ggc cag cac ata gga gag atg agc ttc cta cag cac aac aaa tgt      384
Gln Gly Gln His Ile Gly Glu Met Ser Phe Leu Gln His Asn Lys Cys
            115                 120                 125 gaa tgc aga cca aag aaa gat aga gca aga caa gaa aaa tgt gac aag      432
Glu Cys Arg Pro Lys Lys Asp Arg Ala Arg Gln Glu Lys Cys Asp Lys
130                 135                 140 ccg agg cgg tga                                                      444
Pro Arg Arg
145

<210> SEQ ID NO 2
<211> LENGTH: 147
<212> TYPE: PRT
<213> ORGANISM: Homo sapiens

<400> SEQUENCE: 2

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Cys Asp Lys
130                 135                 140

Pro Arg Arg
145

<210> SEQ ID NO 3
<211> LENGTH: 576
<212> TYPE: DNA
<213> ORGANISM: Homo sapiens
<220> FEATURE:
<221> NAME/KEY: CDS
<222> LOCATION: (1)..(576)
<223> OTHER INFORMATION: VEGF165

<400> SEQUENCE: 3
```

| | | |
|---|---|---|
| atg aac ttt ctg ctg tct tgg gtg cat tgg agc ctt gcc ttg ctg ctc<br>Met Asn Phe Leu Leu Ser Trp Val His Trp Ser Leu Ala Leu Leu Leu<br>1               5                   10                  15 | | 48 |
| tac ctc cac cat gcc aag tgg tcc cag gct gca ccc atg gca gaa gga<br>Tyr Leu His His Ala Lys Trp Ser Gln Ala Ala Pro Met Ala Glu Gly<br>            20                  25                  30 | | 96 |
| gga ggg cag aat cat cac gaa gtg gtg aag ttc atg gat gtc tat cag<br>Gly Gly Gln Asn His His Glu Val Val Lys Phe Met Asp Val Tyr Gln<br>        35                  40                  45 | | 144 |
| cgc agc tac tgc cat cca atc gag acc ctg gtg gac atc ttc cag gag<br>Arg Ser Tyr Cys His Pro Ile Glu Thr Leu Val Asp Ile Phe Gln Glu<br>    50                  55                  60 | | 192 |
| tac cct gat gag atc gag tac atc ttc aag cca tcc tgt gtg ccc ctg<br>Tyr Pro Asp Glu Ile Glu Tyr Ile Phe Lys Pro Ser Cys Val Pro Leu<br>65                  70                  75                  80 | | 240 |
| atg cga tgc ggg ggc tgc tgc aat gac gag ggc ctg gag tgt gtg ccc<br>Met Arg Cys Gly Gly Cys Cys Asn Asp Glu Gly Leu Glu Cys Val Pro<br>                85                  90                  95 | | 288 |
| act gag gag tcc aac atc acc atg cag att atg cgg atc aaa cct cac<br>Thr Glu Glu Ser Asn Ile Thr Met Gln Ile Met Arg Ile Lys Pro His<br>            100                 105                 110 | | 336 |
| caa ggc cag cac ata gga gag atg agc ttc cta cag cac aac aaa tgt<br>Gln Gly Gln His Ile Gly Glu Met Ser Phe Leu Gln His Asn Lys Cys<br>        115                 120                 125 | | 384 |
| gaa tgc aga cca aag aaa gat aga gca aga caa gaa aat ccc tgt ggg<br>Glu Cys Arg Pro Lys Lys Asp Arg Ala Arg Gln Glu Asn Pro Cys Gly<br>    130                 135                 140 | | 432 |
| cct tgc tca gag cgg aga aag cat ttg ttt gta caa gat ccg cag acg<br>Pro Cys Ser Glu Arg Arg Lys His Leu Phe Val Gln Asp Pro Gln Thr<br>145                 150                 155                 160 | | 480 |
| tgt aaa tgt tcc tgc aaa aac aca gac tcg cgt tgc aag gcg agg cag<br>Cys Lys Cys Ser Cys Lys Asn Thr Asp Ser Arg Cys Lys Ala Arg Gln<br>                165                 170                 175 | | 528 |
| ctt gag tta aac gaa cgt act tgc aga tgt gac aag ccg agg cgg tga<br>Leu Glu Leu Asn Glu Arg Thr Cys Arg Cys Asp Lys Pro Arg Arg<br>            180                 185                 190 | | 576 |

<210> SEQ ID NO 4
<211> LENGTH: 191
<212> TYPE: PRT
<213> ORGANISM: Homo sapiens

<400> SEQUENCE: 4

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

```
Glu Cys Arg Pro Lys Lys Asp Arg Ala Arg Gln Glu Asn Pro Cys Gly
        130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
                180                 185                 190

<210> SEQ ID NO 5
<211> LENGTH: 711
<212> TYPE: DNA
<213> ORGANISM: Homo sapiens
<220> FEATURE:
<221> NAME/KEY: CDS
<222> LOCATION: (1)..(711)
<223> OTHER INFORMATION: Fc

<400> SEQUENCE: 5 gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc      96
Pro Glu Leu Leu Gly Gly Pro Ser Val Phe Leu Phe Pro Pro Lys Pro
                20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
            35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
        50                  55                  60 gac ggc gtg gag gtg cat aat gcc aag aca aag ccg cgg gag gag cag     240
Asp Gly Val Glu Val His Asn Ala Lys Thr Lys Pro Arg Glu Glu Gln
65                  70                  75                  80 tac aac agc acg tac cgg gtg gtc agc gtc ctc acc gtc ctg cac cag     288
Tyr Asn Ser Thr Tyr Arg Val Val Ser Val Leu Thr Val Leu His Gln
                85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca gcc ccc atc gag aaa acc atc tcc aaa gcc aaa ggg cag ccc     384
Leu Pro Ala Pro Ile Glu Lys Thr Ile Ser Lys Ala Lys Gly Gln Pro
        115                 120                 125 cga gaa cca cag gtg tac acc ctg ccc cca tcc cgg gat gag ctg acc     432
Arg Glu Pro Gln Val Tyr Thr Leu Pro Pro Ser Arg Asp Glu Leu Thr
130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 aag acc acg cct ccc gtg ctg gac tcc gac ggc tcc ttc ttc ctc tac     576
Lys Thr Thr Pro Pro Val Leu Asp Ser Asp Gly Ser Phe Phe Leu Tyr
            180                 185                 190 agc aag ctc acc gtg gac aag agc agg tgg cag cag ggg aac gtc ttc     624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
```

```
                         210                 215                 220
agc ctc tcc ctg tct ccg ggt aaa gtc gac gag ggc ccg                       711
Ser Leu Ser Leu Ser Pro Gly Lys Val Asp Glu Gly Pro
225                 230                 235

<210> SEQ ID NO 6
<211> LENGTH: 237
<212> TYPE: PRT
<213> ORGANISM: Homo sapiens

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Val Asp Glu Gly Pro
225                 230                 235

<210> SEQ ID NO 7
<211> LENGTH: 5
<212> TYPE: PRT
<213> ORGANISM: Artificial sequence
<220> FEATURE:
<223> OTHER INFORMATION: Synthetic linker

<400> SEQUENCE: 7

Gly Gly Gly Gly Ser
1               5

<210> SEQ ID NO 8
<211> LENGTH: 78
<212> TYPE: DNA
<213> ORGANISM: Artificial sequence
<220> FEATURE:
<223> OTHER INFORMATION: Synthetic polynucleotide
```

```
<220> FEATURE:
<221> NAME/KEY: CDS
<222> LOCATION: (1)..(78)
<223> OTHER INFORMATION: Signal peptide

<400> SEQUENCE: 8 aac ttt ctg ctg tct tgg gtg cat tgg agc ctt gcc ttg ctg ctc tac    48
Asn Phe Leu Leu Ser Trp Val His Trp Ser Leu Ala Leu Leu Leu Tyr
 1               5                  10                  15 ctc cac cat gcc aag tgg tcc cag gct gca                            78
Leu His His Ala Lys Trp Ser Gln Ala Ala
             20                  25

<210> SEQ ID NO 9
<211> LENGTH: 26
<212> TYPE: PRT
<213> ORGANISM: Artificial sequence
<220> FEATURE:
<223> OTHER INFORMATION: Synthetic Construct

<400> SEQUENCE: 9

Asn Phe Leu Leu Ser Trp Val His Trp Ser Leu Ala Leu Leu Leu Tyr
 1               5                  10                  15

Leu His His Ala Lys Trp Ser Gln Ala Ala
             20                  25

<210> SEQ ID NO 10
<211> LENGTH: 2388
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(2388)
<223> OTHER INFORMATION: VEGF121-Fc-linker-Fc-VEGF165-6xHis tag

<400> SEQUENCE: 10 atg aac ttt ctg ctg tct tgg gtg cat tgg agc ctt gcc ttg ctg ctc    48
Met Asn Phe Leu Leu Ser Trp Val His Trp Ser Leu Ala Leu Leu Leu
 1               5                  10                  15 tac ctc cac cat gcc aag tgg tcc cag gct gca ccc atg gca gaa gga    96
Tyr Leu His His Ala Lys Trp Ser Gln Ala Ala Pro Met Ala Glu Gly
             20                  25                  30 gga ggg cag aat cat cac gaa gtg gtg aag ttc atg gat gtc tat cag   144
Gly Gly Gln Asn His His Glu Val Val Lys Phe Met Asp Val Tyr Gln
         35                  40                  45 cgc agc tac tgc cat cca atc gag acc ctg gtg gac atc ttc cag gag   192
Arg Ser Tyr Cys His Pro Ile Glu Thr Leu Val Asp Ile Phe Gln Glu
     50                  55                  60 tac cct gat gag atc gag tac atc ttc aag cca tcc tgt gtg ccc ctg   240
Tyr Pro Asp Glu Ile Glu Tyr Ile Phe Lys Pro Ser Cys Val Pro Leu
65                  70                  75                  80 atg cga tgc ggg ggc tgc tgc aat gac gag ggc ctg gag tgt gtg ccc   288
Met Arg Cys Gly Gly Cys Cys Asn Asp Glu Gly Leu Glu Cys Val Pro
                 85                  90                  95 act gag gag tcc aac atc acc atg cag att atg cgg atc aaa cct cac   336
Thr Glu Glu Ser Asn Ile Thr Met Gln Ile Met Arg Ile Lys Pro His
            100                 105                 110 caa ggc cag cac ata gga gag atg agc ttc cta cag cac aac aaa tgt   384
Gln Gly Gln His Ile Gly Glu Met Ser Phe Leu Gln His Asn Lys Cys
        115                 120                 125 gaa tgc aga cca aag aaa gat gag ccc aaa tct tgt gac aaa act cac   432
Glu Cys Arg Pro Lys Lys Asp Glu Pro Lys Ser Cys Asp Lys Thr His
```

-continued

```
              130                 135                 140
aca tgc cca ccg tgc cca gca cct gaa ctc ctg ggg gga ccg tca gtc    480
Thr Cys Pro Pro Cys Pro Ala Pro Glu Leu Leu Gly Gly Pro Ser Val
145                 150                 155                 160 ttc ctc ttc ccc cca aaa ccc aag gac acc ctc atg atc tcc cgg acc    528
Phe Leu Phe Pro Pro Lys Pro Lys Asp Thr Leu Met Ile Ser Arg Thr
                165                 170                 175 cct gag gtc aca tgc gtg gtg gtg gac gtg agc cac gaa gac cct gag    576
Pro Glu Val Thr Cys Val Val Val Asp Val Ser His Glu Asp Pro Glu
            180                 185                 190 gtc aag ttc aac tgg tac gtg gac ggc gtg gag gtg cat aat gcc aag    624
Val Lys Phe Asn Trp Tyr Val Asp Gly Val Glu Val His Asn Ala Lys
        195                 200                 205 aca aag ccg cgg gag gag cag tac aac agc acg tac cgg gtg gtc agc    672
Thr Lys Pro Arg Glu Glu Gln Tyr Asn Ser Thr Tyr Arg Val Val Ser
    210                 215                 220 gtc ctc acc gtc ctg cac cag gac tgg ctg aat ggc aag gag tac aag    720
Val Leu Thr Val Leu His Gln Asp Trp Leu Asn Gly Lys Glu Tyr Lys
225                 230                 235                 240 tgc aag gtc tcc aac aaa gcc ctc cca gcc ccc atc gag aaa acc atc    768
Cys Lys Val Ser Asn Lys Ala Leu Pro Ala Pro Ile Glu Lys Thr Ile
                245                 250                 255 tcc aaa gcc aaa ggg cag ccc cga gaa cca cag gtg tac acc ctg ccc    816
Ser Lys Ala Lys Gly Gln Pro Arg Glu Pro Gln Val Tyr Thr Leu Pro
            260                 265                 270 cca tcc cgg gat gag ctg acc aag aac cag gtc agc ctg acc tgc ctg    864
Pro Ser Arg Asp Glu Leu Thr Lys Asn Gln Val Ser Leu Thr Cys Leu
        275                 280                 285 gtc aaa ggc ttc tat ccc agc gac atc gcc gtg gag tgg gag agc aat    912
Val Lys Gly Phe Tyr Pro Ser Asp Ile Ala Val Glu Trp Glu Ser Asn
    290                 295                 300 ggg cag ccg gag aac aac tac aag acc acg cct ccc gtg ctg gac tcc    960
Gly Gln Pro Glu Asn Asn Tyr Lys Thr Thr Pro Pro Val Leu Asp Ser
305                 310                 315                 320 gac ggc tcc ttc ttc ctc tac agc aag ctc acc gtg gac aag agc agg   1008
Asp Gly Ser Phe Phe Leu Tyr Ser Lys Leu Thr Val Asp Lys Ser Arg
                325                 330                 335 tgg cag cag ggg aac gtc ttc tca tgc tcc gtg atg cat gag gct ctg   1056
Trp Gln Gln Gly Asn Val Phe Ser Cys Ser Val Met His Glu Ala Leu
            340                 345                 350 cac aac cac tac acg cag aag agc ctc tcc ctg tct ccg ggt aaa gtc   1104
His Asn His Tyr Thr Gln Lys Ser Leu Ser Leu Ser Pro Gly Lys Val
        355                 360                 365 gac gag ggc ccg ggt gga ggc ggg tcg ggc ggt ggg gga tct ggg ggc   1152
Asp Glu Gly Pro Gly Gly Gly Gly Ser Gly Gly Gly Gly Ser Gly Gly
    370                 375                 380 ggt gga tcc gag ccc aaa tct tgt gac aaa act cac aca tgc cca ccg   1200
Gly Gly Ser Glu Pro Lys Ser Cys Asp Lys Thr His Thr Cys Pro Pro
385                 390                 395                 400 tgc cca gca cct gaa ctc ctg ggg gga ccg tca gtc ttc ctc ttc ccc   1248
Cys Pro Ala Pro Glu Leu Leu Gly Gly Pro Ser Val Phe Leu Phe Pro
                405                 410                 415 cca aaa ccc aag gac acc ctc atg atc tcc cgg acc cct gag gtc aca   1296
Pro Lys Pro Lys Asp Thr Leu Met Ile Ser Arg Thr Pro Glu Val Thr
            420                 425                 430 tgc gtg gtg gtg gac gtg agc cac gaa gac cct gag gtc aag ttc aac   1344
Cys Val Val Val Asp Val Ser His Glu Asp Pro Glu Val Lys Phe Asn
        435                 440                 445 tgg tac gtg gac ggc gtg gag gtg cat aat gcc aag aca aag ccg cgg   1392
Trp Tyr Val Asp Gly Val Glu Val His Asn Ala Lys Thr Lys Pro Arg
```

-continued

```
Trp Tyr Val Asp Gly Val Glu Val His Asn Ala Lys Thr Lys Pro Arg
    450             455                 460 gag gag cag tac aac agc acg tac cgg gtg gtc agc gtc ctc acc gtc      1440
Glu Glu Gln Tyr Asn Ser Thr Tyr Arg Val Val Ser Val Leu Thr Val
465                 470                 475                 480 ctg cac cag gac tgg ctg aat ggc aag gag tac aag tgc aag gtc tcc      1488
Leu His Gln Asp Trp Leu Asn Gly Lys Glu Tyr Lys Cys Lys Val Ser
                    485                 490                 495 aac aaa gcc ctc cca gcc ccc atc gag aaa acc atc tcc aaa gcc aaa      1536
Asn Lys Ala Leu Pro Ala Pro Ile Glu Lys Thr Ile Ser Lys Ala Lys
                500                 505                 510 ggg cag ccc cga gaa cca cag gtg tac acc ctg ccc cca tcc cgg gat      1584
Gly Gln Pro Arg Glu Pro Gln Val Tyr Thr Leu Pro Pro Ser Arg Asp
            515                 520                 525 gag ctg acc aag aac cag gtc agc ctg acc tgc ctg gtc aaa ggc ttc      1632
Glu Leu Thr Lys Asn Gln Val Ser Leu Thr Cys Leu Val Lys Gly Phe
        530                 535                 540 tat ccc agc gac atc gcc gtg gag tgg gag agc aat ggg cag ccg gag      1680
Tyr Pro Ser Asp Ile Ala Val Glu Trp Glu Ser Asn Gly Gln Pro Glu
545                 550                 555                 560 aac aac tac aag acc acg cct ccc gtg ctg gac tcc gac ggc tcc ttc      1728
Asn Asn Tyr Lys Thr Thr Pro Pro Val Leu Asp Ser Asp Gly Ser Phe
                565                 570                 575 ttc ctc tac agc aag ctc acc gtg gac aag agc agg tgg cag cag ggg      1776
Phe Leu Tyr Ser Lys Leu Thr Val Asp Lys Ser Arg Trp Gln Gln Gly
            580                 585                 590 aac gtc ttc tca tgc tcc gtg atg cat gag gct ctg cac aac cac tac      1824
Asn Val Phe Ser Cys Ser Val Met His Glu Ala Leu His Asn His Tyr
        595                 600                 605 acg cag aag agc ctc tcc ctg tct ccg ggt aaa gtc gac gag ggc ccg      1872
Thr Gln Lys Ser Leu Ser Leu Ser Pro Gly Lys Val Asp Glu Gly Pro
610                 615                 620 gca ccc atg gca gaa gga gga ggg cag aat cat cac gaa gtg gtg aag      1920
Ala Pro Met Ala Glu Gly Gly Gly Gln Asn His His Glu Val Val Lys
625                 630                 635                 640 ttc atg gat gtc tat cag cgc agc tac tgc cat cca atc gag acc ctg      1968
Phe Met Asp Val Tyr Gln Arg Ser Tyr Cys His Pro Ile Glu Thr Leu
                645                 650                 655 gtg gac atc ttc cag gag tac cct gat gag atc gag tac atc ttc aag      2016
Val Asp Ile Phe Gln Glu Tyr Pro Asp Glu Ile Glu Tyr Ile Phe Lys
            660                 665                 670 cca tcc tgt gtg ccc ctg atg cga tgc ggg ggc tgc tgc aat gac gag      2064
Pro Ser Cys Val Pro Leu Met Arg Cys Gly Gly Cys Cys Asn Asp Glu
        675                 680                 685 ggc ctg gag tgt gtg ccc act gag gag tcc aac atc acc atg cag att      2112
Gly Leu Glu Cys Val Pro Thr Glu Glu Ser Asn Ile Thr Met Gln Ile
690                 695                 700 atg cgg atc aaa cct cac caa ggc cag cac ata gga gag atg agc ttc      2160
Met Arg Ile Lys Pro His Gln Gly Gln His Ile Gly Glu Met Ser Phe
705                 710                 715                 720 cta cag cac aac aaa tgt gaa tgc aga cca aag aaa gat aga gca aga      2208
Leu Gln His Asn Lys Cys Glu Cys Arg Pro Lys Lys Asp Arg Ala Arg
                725                 730                 735 caa gaa aat ccc tgt ggg cct tgc tca gag cgg aga aag cat ttg ttt      2256
Gln Glu Asn Pro Cys Gly Pro Cys Ser Glu Arg Arg Lys His Leu Phe
            740                 745                 750 gta caa gat ccg cag acg tgt aaa tgt tcc tgc aaa aac aca gac tcg      2304
Val Gln Asp Pro Gln Thr Cys Lys Cys Ser Cys Lys Asn Thr Asp Ser
        755                 760                 765
```

```
cgt tgc aag gcg agg cag ctt gag tta aac gaa cgt act tgc aga tgt    2352
Arg Cys Lys Ala Arg Gln Leu Glu Leu Asn Glu Arg Thr Cys Arg Cys
770                 775                 780 gac aag ccg agg cgg cac cac cac cac cac cac tga                    2388
Asp Lys Pro Arg Arg His His His His His His
785                 790                 795
```

<210> SEQ ID NO 11
<211> LENGTH: 795
<212> TYPE: PRT
<213> ORGANISM: Artificial sequence
<220> FEATURE:
<223> OTHER INFORMATION: Synthetic Construct

<400> SEQUENCE: 11

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Glu Pro Lys Ser Cys Asp Lys Thr His
    130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
        275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
```

```
                    325                 330                 335
Trp Gln Gln Gly Asn Val Phe Ser Cys Ser Val Met His Glu Ala Leu
            340                 345                 350
His Asn His Tyr Thr Gln Lys Ser Leu Ser Leu Ser Pro Gly Lys Val
            355                 360                 365
Asp Glu Gly Pro Gly Gly Gly Ser Gly Gly Gly Ser Gly Gly
        370                 375                 380
Gly Gly Ser Glu Pro Lys Ser Cys Asp Lys Thr His Thr Cys Pro Pro
385                 390                 395                 400
Cys Pro Ala Pro Glu Leu Leu Gly Gly Pro Ser Val Phe Leu Phe Pro
                405                 410                 415
Pro Lys Pro Lys Asp Thr Leu Met Ile Ser Arg Thr Pro Glu Val Thr
            420                 425                 430
Cys Val Val Val Asp Val Ser His Glu Asp Pro Glu Val Lys Phe Asn
                435                 440                 445
Trp Tyr Val Asp Gly Val Glu Val His Asn Ala Lys Thr Lys Pro Arg
        450                 455                 460
Glu Glu Gln Tyr Asn Ser Thr Tyr Arg Val Val Ser Val Leu Thr Val
465                 470                 475                 480
Leu His Gln Asp Trp Leu Asn Gly Lys Glu Tyr Lys Cys Lys Val Ser
                485                 490                 495
Asn Lys Ala Leu Pro Ala Pro Ile Glu Lys Thr Ile Ser Lys Ala Lys
            500                 505                 510
Gly Gln Pro Arg Glu Pro Gln Val Tyr Thr Leu Pro Pro Ser Arg Asp
        515                 520                 525
Glu Leu Thr Lys Asn Gln Val Ser Leu Thr Cys Leu Val Lys Gly Phe
    530                 535                 540
Tyr Pro Ser Asp Ile Ala Val Glu Trp Glu Ser Asn Gly Gln Pro Glu
545                 550                 555                 560
Asn Asn Tyr Lys Thr Thr Pro Pro Val Leu Asp Ser Asp Gly Ser Phe
                565                 570                 575
Phe Leu Tyr Ser Lys Leu Thr Val Asp Lys Ser Arg Trp Gln Gln Gly
            580                 585                 590
Asn Val Phe Ser Cys Ser Val Met His Glu Ala Leu His Asn His Tyr
        595                 600                 605
Thr Gln Lys Ser Leu Ser Leu Ser Pro Gly Lys Val Asp Glu Gly Pro
    610                 615                 620
Ala Pro Met Ala Glu Gly Gly Gly Gln Asn His His Glu Val Val Lys
625                 630                 635                 640
Phe Met Asp Val Tyr Gln Arg Ser Tyr Cys His Pro Ile Glu Thr Leu
                645                 650                 655
Val Asp Ile Phe Gln Glu Tyr Pro Asp Glu Ile Glu Tyr Ile Phe Lys
            660                 665                 670
Pro Ser Cys Val Pro Leu Met Arg Cys Gly Gly Cys Cys Asn Asp Glu
        675                 680                 685
Gly Leu Glu Cys Val Pro Thr Glu Glu Ser Asn Ile Thr Met Gln Ile
    690                 695                 700
Met Arg Ile Lys Pro His Gln Gly Gln His Ile Gly Glu Met Ser Phe
705                 710                 715                 720
Leu Gln His Asn Lys Cys Glu Cys Arg Pro Lys Lys Asp Arg Ala Arg
                725                 730                 735
Gln Glu Asn Pro Cys Gly Pro Cys Ser Glu Arg Arg Lys His Leu Phe
            740                 745                 750
```

```
Val Gln Asp Pro Gln Thr Cys Lys Cys Ser Cys Lys Asn Thr Asp Ser
        755                 760                 765

Arg Cys Lys Ala Arg Gln Leu Glu Leu Asn Glu Arg Thr Cys Arg Cys
        770                 775                 780

Asp Lys Pro Arg Arg His His His His His
785                 790             795
```

HETERODIMERIC VASCULAR ENDOTHELIAL GROWTH FACTOR AND USE THEREOF

CROSS-REFERENCE TO RELATED APPLICATIONS

This application is the National Stage of International Application No. PCT/US2016/064554, filed on Dec. 2, 2016, which claims the benefit of U.S. Provisional Application No. 62/262,630, filed on Dec. 3, 2015. The contents of both applications are hereby incorporated by reference in their entirety.

BACKGROUND

Angiogenesis is a critical rate-limiting process during tumor progression, which is induced by tilting the balance toward proangiogenic factors to drive vascular growth. Cancer cells in a microenvironment count on angiogenesis to supply oxygen and nutrients. Thus, agents targeting angiogenic pathways have been investigated as potential cancer drugs. Initial efforts have primarily focused on targeting endothelial and tumor-derived vascular endothelial growth factor A (VEGF-A)/VEGFR signaling. Several different strategies have been designed to inhibit this signaling as monotherapy or adjuvant therapies, e.g., small molecules inhibitors of VEGFR signaling, VEGF-Trap, anti-VEGFR antibodies, and the anti-VEGF-A monoclonal antibody Bevacizumab (Avastin), the first VEGF-A targeted antibody approved by the US FDA in 2004.

However, a significant number of patients either do not respond to antiangiogenic agents or rapidly develop resistance to them. Tumors may develop resistance to antiangiogenic agents via adaptive responses, e.g., upregulating alternative proangiogenic signaling, co-opting normal peritumoral blood vessels, suppressing immune surveillance by recruiting immune cells and bone-marrow-derived proangiogenic cells, and activating invasiveness phenotype. These adaptive responses are induced by intratumoral hypoxia that results from tumor vessel pruning and extensive suppression of angiogenesis.

It remains a major challenge to efficiently inhibit VEGF-A/VEGFR signaling and, at the same time, alleviate resistance to antiangiogenic therapy.

SUMMARY

In one aspect, provided herein is a fusion protein that contains (i) a first vascular endothelial growth factor (VEGF) isoform, and (ii) a second VEGF isoform, and (iii) a dimerization domain between the first isoform and the second isoform. The first isoform and the second isoform are selected from $VEGF_{121}$ and $VEGF_{165}$. $VEGF_{121}$ can have an amino acid sequence that is at least 80% (e.g., at least 99%, 98%, 97%, 96%, 95%, 90%, or 85%) identical to the sequence of SEQ ID NO: 2. $VEGF_{165}$ can have an amino acid sequence that is at least 80% (e.g., at least 99%, 98%, 97%, 96%, 95%, 90%, or 85%) identical to the sequence of SEQ ID NO: 4.

In one embodiment, the dimerization domain contains two Fc regions and a linker between the two Fc regions. The linker can be a flexible linker consisting of 15 to 30 amino acids. For example, the linker can be (Gly-Gly-Gly-Gly-Ser)$_n$, n being 3, 4, 5, or 6.

In one embodiment, the fusion protein includes, in the direction from the N-terminus to the C-terminus, $VEGF_{121}$, one of the two Fc regions, the linker, the other of the two Fc regions, and $VEGF_{165}$.

In another embodiment, the fusion protein contains, in the direction from the N-terminus to the C-terminus, $VEGF_{165}$, one of the two Fc regions, the linker, the other of the two Fc regions, and $VEGF_{121}$.

The fusion protein can have an amino acid sequence that is at least 80% (e.g., identical to the sequence of SEQ ID NO: 11.

In another aspect, provided herein is a nucleic acid molecule that includes a nucleic acid sequence encoding the fusion protein described in this disclosure. In one embodiment, the nucleic acid sequence encodes an amino acid sequence that is at least 80% (e.g., at least 99%, 98%, 97%, 96%, 95%, 90%, or 85%) identical to the sequence of SEQ ID NO: 11.

In yet another aspect, provided herein is a pharmaceutical composition that contains the fusion protein and a pharmaceutically acceptable carrier. The pharmaceutical composition can be used to treat cancer or inhibit angiogenesis in a subject in need thereof.

The details of one or more embodiments are set forth in the accompanying drawing and the description below. Other features, objects, and advantages of the embodiments will be apparent from the description and drawing, and from the claims.

DETAILED DESCRIPTION

It was surprisingly discovered that a heterodimeric vascular endothelial growth factor (VEGF) composed of two different VEGF isoforms reduced proliferation, migration, invasion, and tube formation in endothelial and cancer cells through competing with $VEGF_{165}$ homodimer in a paracrine and an autocrine manner Therefore, described herein is a fusion VEGF protein containing isoform $VEGF_{121}$ and isoform $VEGF_{165}$ linked by a dimerization domain.

Figure 1:
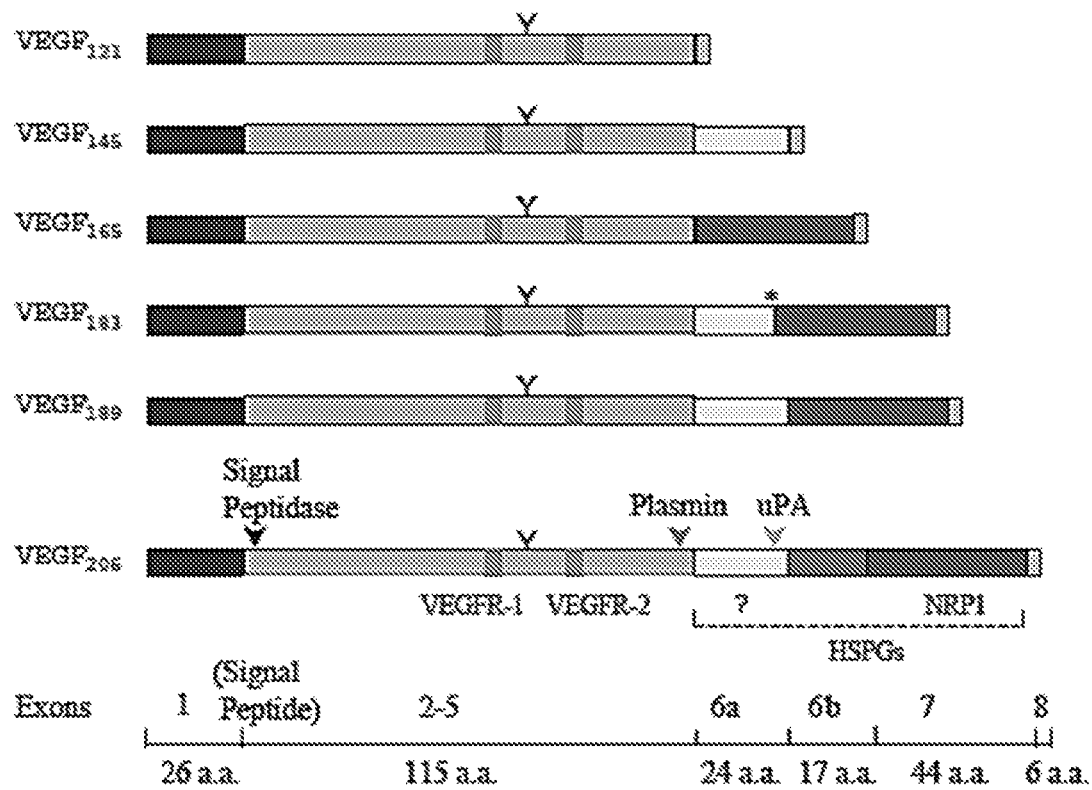
FIG. 1 is a schematic representation of the VEGF isoforms.

The VEGF-A gene includes eight exons, which can give rise to alternatively spliced variants, i.e., $VEGF_{121}$, $VEGF_{145}$, $VEGF_{165}$, $VEGF_{183}$, $VEGF_{189}$, and $VEGF_{206}$. See FIG. 1

$VEGF_{121}$ is a freely soluble and weakly acidic polypeptide that lacks a heparin-binding domain. A $VEGF_{121}$ nucleic acid sequence (SEQ ID NO: 1) and the amino acid sequence it encodes (SEQ ID NO: 2) are provided herewith. The sequence of SEQ ID NO: 2 includes an N-terminal signal peptide, which is not present in the mature form of $VEGF_{121}$.

$VEGF_{165}$ contains basic amino acids and a heparin-binding domain that binds the VEGF receptor to induce signal transduction and stimulate endothelial cell proliferation. A $VEGF_{165}$ nucleic acid sequence (SEQ ID NO: 3) and the amino acid sequence it encodes (SEQ ID NO: 4) are provided herewith. The sequence of SEQ ID NO: 4 includes an N-terminal signal peptide, which is not present in the mature form of $VEGF_{165}$.

The fusion VEGF further includes a dimerization domain positioned in between the two VEGF isoforms such that the fusion VEFG forms a heterodimer. In one embodiment, the dimerization domain consists of two Fc regions linked by a linker. The Fc region can be a human IgG Fc region. For example, the Fc region can have the amino acid sequence of SEQ ID NO: 6, which is encoded by the nucleic acid sequence of SEQ ID NO: 5.

The linker between the two Fc regions can be any flexible linker known in the art. The linker can have between 15 and 30 amino acids. A flexible linker can be a Gly- and Ser-rich linker. For example, the linker can be (Gly-Gly-Gly-Gly-Ser)$_n$ (SEQ ID NO:7), n being an integer (e.g., 1, 2, 3, 4, 5, 6, 7, or 8).

The fusion protein can further include a signal peptide at the N-terminus. The signal peptide can be the signal peptide endogenous to the VEGF isoforms. For example, the signal peptide can have the sequence of SEQ ID NO: 9 (encoded by the nucleic acid sequence of SEQ ID NO: 8). The C-terminal VEGF isoform in the fusion protein may or may not include a signal peptide.

In addition, the fusion protein can include a C-terminal tag to facilitate isolation or identification of the fusion protein. Such tag can be a poly(His) tag, HA tag, Myc tag, V5, or FLAG tag.

The fusion protein can contain, in the direction from the N-terminus to the C-terminus, $VEGF_{165}$, an Fc region, a linker, an Fc region, and $VEGF_{121}$. Alternatively, the fusion protein can contain, in the direction from the N-terminus to the C-terminus, $VEGF_{121}$, an Fc region, a linker, an Fc region, and $VEGF_{165}$. Each isoform can be linked to an Fc region directly or indirectly via a linker, which can be different or identical to the linker between the two Fc regions. In one embodiment, the fusion protein has an amino acid sequence that is at least 80% (e.g., at least 99%, 98%, 97%, 96%, 95%, 90%, or 85%) identical to the sequence of SEQ ID NO: 11, which is encoded by the sequence of SEQ ID NO: 10.

Conventional methods, e.g., recombinant technology, can be used to make the fusion protein. For example, an expression construct encoding the protein can be generated and introduced into suitable host cells (e.g., mammalian cells). The fusion protein expressed in the host cells can then be isolated.

The fusion protein can be mixed with a pharmaceutically acceptable carrier to form a pharmaceutical composition. The composition can be administered to a subject in need thereof to treat cancer or inhibit angiogenesis. The fusion protein can also be used in a combination therapy with other cancer treatments.

The fusion protein can also be conjugated to or encapsulated in moieties (e.g., lipids, carbohydrates, polymers or nanoparticles) designed to target the fusion protein to tumors and/or their associated vasculature.

The composition can be formulated with a pharmaceutically acceptable carrier such as a phosphate buffered saline, a bicarbonate solution, and/or an adjuvant. Suitable pharmaceutical carriers and diluents, as well as pharmaceutical necessities for their use, are known in the art. This composition may be prepared as an injectable, liquid solution, emulsion, or another suitable formulation.

Examples of adjuvants include, but are not limited to, alum-precipitate, Freund's complete adjuvant, Freund's incomplete adjuvant, monophosphoryl-lipid A/trehalose dicorynomycolate adjuvant, water in oil emulsion containing Corynebacterium parvum and tRNA, and other substances that accomplish the task of increasing immune response by mimicking specific sets of evolutionarily conserved molecules including liposomes, lipopolysaccharide (LPS), molecular cages for antigen, components of bacterial cell walls, and endocytosed nucleic acids such as double-stranded RNA, single-stranded DNA, and unmethylated CpG dinucleotide-containing DNA. Other examples include cholera toxin, E. coli heat-labile enterotoxin, liposome, immune-stimulating complex (ISCOM), immunostimulatory sequences oligodeoxynucleotide, and aluminum hydroxide. The composition can also include a polymer that facilitates in vivo delivery.

An effective amount of the composition described above may be administered parenterally, e.g., subcutaneous injection, intravenous injection, or intramuscular injection. Other routes of administration may also be used. A skilled practitioner would be able to determine the appropriate dosage and route of administration.

Cancers that can be treated with the fusion protein include solid tumors such as glioblastoma, colorectal cancer, lung cancer, renal cancer, liver cancer, kidney cancer, neuroendocrine tumors, breast cancer, esophageal cancer, gastrointestinal stromal tumors, melanoma, ovarian cancer, cervical cancer, pancreatic cancer, prostate cancer, stomach cancer, and head and neck cancer.

The specific example below is to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are hereby incorporated by reference in their entirety.

EXAMPLE

We generated a novel chimeric dimer of $VEGF_{121}$-$VEGF_{165}$ fused with two Fc regions of human IgG1 as a powerful antiangiogenic modulator. It was found that the chimeric $VEGF_{121}$-$VEGF_{165}$ recombinant protein reduced tube formation of 3B-11 endothelial cells and inhibited invasiveness of HCT-15 cancer cells. Furthermore, we found that the $VEGF_{121}$-$VEGF_{165}$ protein attenuated VEGFR2-HIF-1α signaling through the PI3K-AKT-mTOR pathway in cancer cells. The data demonstrated that the chimeric $VEGF_{121}$-$VEGF_{165}$ protein antagonizes angiogenesis and HIF-1α signaling, and suggested that it could combat drug resistance to antiangiogenic therapy.

Construction and characterization of a $VEGF_{121}$-$VEGF_{165}$ fusion protein

Figure 2:
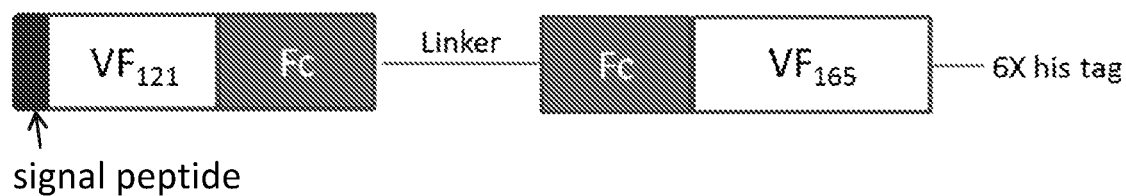
FIG. 2 is a schematic representation of a $VEGF_{121}$–$VEGF_{165}$ fusion protein

A $VEGF_{121}$-$VEGF_{165}$ fusion was generated by fusing a human IgG1 Fc nucleic acid sequence to the 3' terminus of a $VEGF_{121}$ sequence and the 5' terminus of a $VEGF_{165}$ sequence, respectively, and the two Fc sequences were connected by a linker sequence. The $VEGF_{121}$-$VEGF_{165}$ fusion nucleic acid sequence was cloned into the pcDNA3.1 vector, yielding the expression vector for $VEGF_{121}$-$VEGF_{165}$. The integrity of the final construct was confirmed by DNA sequencing. The deduced protein includes a putative 26-aa signal peptide. See FIG. 2. The plasmid containing the $VEGF_{121}$-$VEGF_{165}$ fusion gene was transfected into 293T cell line. The expression and secretion of $VEGF_{121}$-$VEGF_{165}$ fusion protein were confirmed by Western blot. We found a single band of ~120 kDa for $VEGF_{121}$-$VEGF_{165}$ fusion protein in samples from cultured medium and cell lysates of transfected 293T cells (data not shown). The recombinant protein $VEGF_{121}$-$VEGF_{165}$ was expressed as a His-tag fusion protein in 293T cells and purified using nickel affinity chromatography. The purity and the molecular weight of the purified fusion protein were determined by Western blot (data not shown). These results indicated that $VEGF_{121}$-$VEGF_{165}$ formed a dimer covalently linked by IgG1 Fc fragments and a polypeptide linker.

Figure 3:
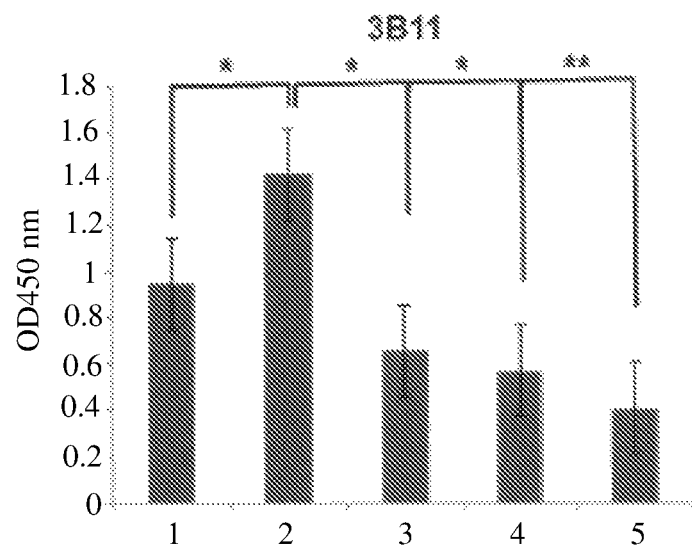
FIG. 3 is a set of graphs showing the effect of the $VEGF_{121}$–$VEGF_{165}$ protein on cell proliferation. A total of $1 \times 10^4$ 3B-11 cells (A) and HCT-15 cells (B) were treated with the fusion protein (42, 83, 125 pM) in the presence of $VEGF_{165}$ (222 pM). Cell proliferation was measured by a CCK-8 kit (t-test, *P<0.05, **P<0.01, n=3). 1: Control; 2: $VEGF_{165}$; 3: $VEGF_{165}$+$VEGF_{121}$–$VEGF_{165}$ (42 pM); 4: $VEGF_{165}$+$VEGF_{121}$–$VEGF_{165}$ (83 pM); 5: $VEGF_{165}$+$VEGF_{121}$–$VEGF_{165}$ (125 pM).
Figure 3:
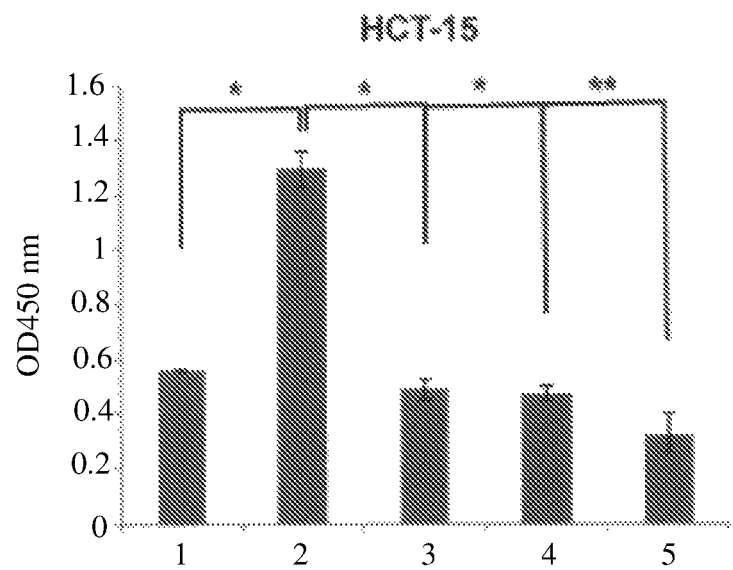

$VEGF_{121}$-$VEGF_{165}$ fusion protein inhibited cell proliferation induced by $VEGF_{165}$ Since endothelial cell proliferation is required for early angiogenic response, we examined whether the $VEGF_{121}$-$VEGF_{165}$ protein affected proliferation of $VEGF_{165}$-stimulated 3B-11 cells, a convenient endothelial cell model for tube formation assay. See Zhou et al., Methods 2008, 44(2):190-195. $VEGF_{165}$-induced cell growth of 3B-11 was blocked in a concentration-dependent manner by $VEGF_{121}$-$VEGF_{165}$. See FIG. 3, panel A. The effect of $VEGF_{165}$ at a concentration of 222 pM on 3B-11 cell proliferation was easily inhibited by the recombinant $VEGF_{121}$-$VEGF_{165}$ at 42 pM, suggesting that the $VEGF_{121}$-$VEGF_{165}$ protein was able to efficiently block the activity of $VEGF_{165}$-induced proliferation. Moreover, the $VEGF_{121}$-$VEGF_{165}$ protein exhibited similar potency at inhibiting $VEGF_{165}$-induced growth of HCT-15 cancer cells. See FIG. 3, panel B. We also found that $VEGF_{121}$-$VEGF_{165}$ exhibited similar activity in inhibiting cell proliferation of 3B-11 and HCT-15 cells in an autocrine manner when the plasmid of the fusion gene was transfected into these cells, although the inhibition was not statistically significant (data not shown). The results suggest that $VEGF_{121}$-$VEGF_{165}$ inhibit the increase in cell number due to suppression of proliferation, not cytotoxicity. Furthermore, $VEGF_{121}$-$VEGF_{165}$ inhibited cell transformation of HCT-15 in an autocrine manner (data not shown). Our results indicate that the $VEGF_{121}$-$VEGF_{165}$ recombinant protein can block cell proliferation of 3B-11 as well as cell proliferation and transformation of colon cancer cell HCT-15 in autocrine and paracrine manners.

$VEGF_{121}$-$VEGF_{165}$ fusion protein inhibited tube formation induced by $VEGF_{165}$ Later stages of angiogenesis require morphological alterations of endothelial cells, which result in lumen formation. We examined tube formation in vitro in the presence of the $VEGF_{121}$-$VEGF_{165}$ protein. An in vitro tube formation assay was employed by using 3B-11 endothelial cells that were induced to invade a three-dimensional collagen gel where they formed a network of capillary-like tubes. See Zhou et al., Methods 2008, 44(2):190-195.

Figure 4:
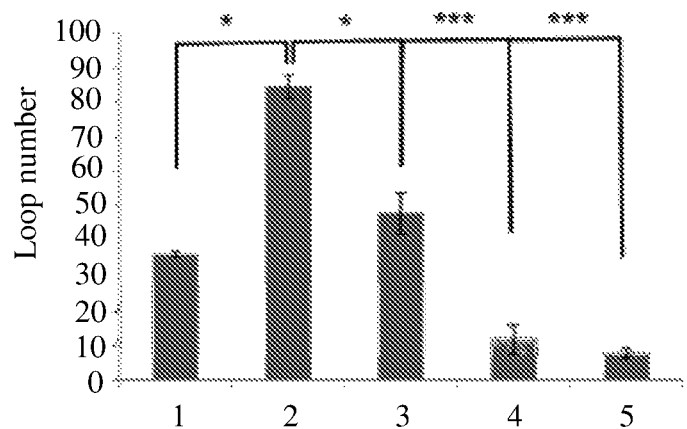
FIG. 4 is a set of graphs showing the effect of the $VEGF_{121}$–$VEGF_{165}$ protein on tube formation. (A) 3B-11 ($8 \times 10^5$) cells were inoculated on Matrigel and treated with $VEGF_{121}$–$VEGF_{165}$ (42, 83, 125 pM) in the presence of $VEGF_{165}$ (222 pM). Tube formation was quantified by counting the connected cells in randomly selected fields at 100× magnification. 1: Control; 2: $VEGF_{165}$; 3: $VEGF_{165}$+$VEGF_{121}$–$VEGF_{165}$ (42 pM); 4: $VEGF_{165}$+$VEGF_{121}$–$VEGF_{165}$ (83 pM); 5: $VEGF_{165}$+$VEGF_{121}$–$VEGF_{165}$ (125 pM). (B) $VEGF_{121}$–$VEGF_{165}$ plasmid was transfected into 3B-11 cells. Tube formation assay was carried out using the 3B-11 cells. Data are presented as the means±SEM based on three independent experiments. 1: Control; 2: $VEGF_{165}$ (222 pM); 3: $VEGF_{121}$–$VEGF_{165}$ plasmid. *P<0.05, P<0.01, *p<0.001.
Figure 4:
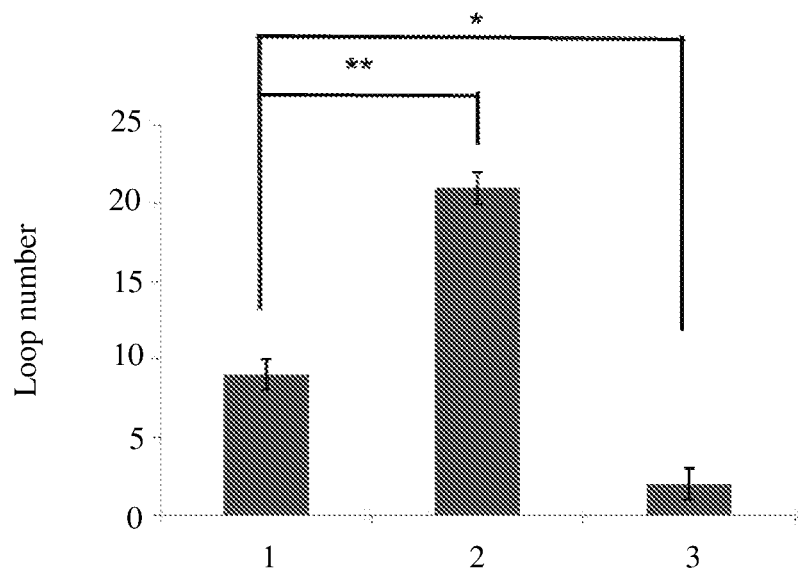

The results showed that 3B-11 cells could form a tube network under normal condition, and $VEGF_{165}$ increases numbers of tube formation. See FIG. 4, panel A. However, the numbers of tube-like structure formation in 3B-11 cells were inhibited by the addition of the $VEGF_{121}$-$VEGF_{165}$ protein in a concentration-dependent manner See FIG. 4, panel A. Furthermore, the $VEGF_{121}$-$VEGF_{165}$ protein significantly inhibited $VEGF_{165}$-induced tube formation in a paracrine manner (FIG. 4, A) and in an autocrine manner (FIG. 4, B). These results demonstrated that the $VEGF_{121}$-$VEGF_{165}$ chimeric protein can inhibit $VEGF_{165}$-induced angiogenesis in vitro.

$VEGF_{121}$-$VEGF_{165}$ fusion protein inhibited cell migration

Figure 5:
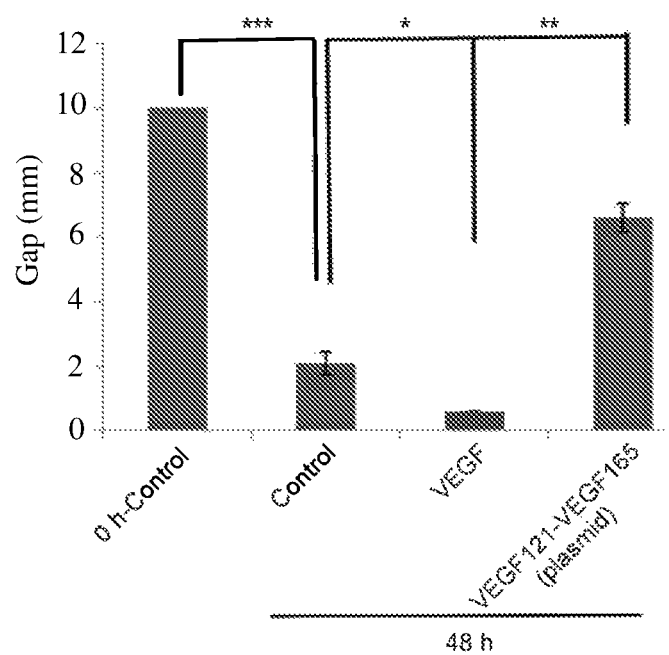
FIG. 5 is a graph showing the effect of the $VEGF_{121}$–$VEGF_{165}$ protein on 3B-11 cell migration. $VEGF_{121}$–$VEGF_{165}$ plasmid was transfected into 3B-11 cells. Cell migration was determined using the transfected 3B-11 cells. Cell migration ability of 3B-11 cells was enhanced in the presence of $VEGF_{165}$ (222 pM) but inhibited by the presence of the $VEGF_{121}$–$VEGF_{165}$ plasmid.
Figure 6:
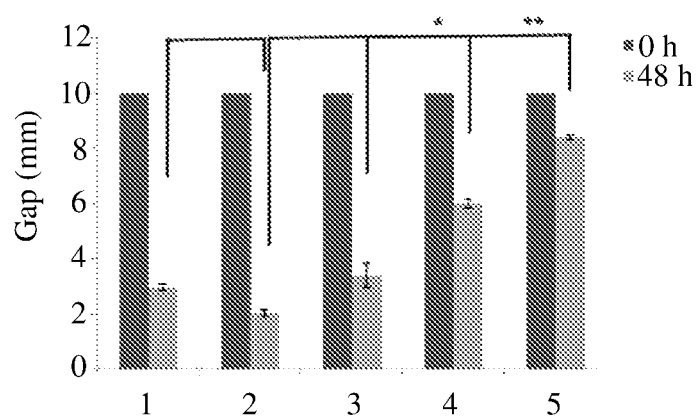
FIG. 6 is a set of graphs showing the effect of the $VEGF_{121}$–$VEGF_{165}$ protein on HCT-15 cell migration. (A) HCT-15 cells were inoculated in Transwell™ permeable inserts and treated with the $VEGF_{121}$–$VEGF_{165}$ protein (42, 83, 125 pM) or in the presence of $VEGF_{165}$ (222 pM). The distance between the gap was analyzed in Transwell™ permeable inserts. Untreated HCT-15 cells were used as controls. 1: Control; 2: $VEGF_{165}$; 3: $VEGF_{165}$+$VEGF_{121}$–$VEGF_{165}$ (42 pM); 4: $VEGF_{165}$+$VEGF_{121}$–$VEGF_{165}$ (83 pM); 5: $VEGF_{165}$+$VEGF_{121}$–$VEGF_{165}$ (125 pM). (B) $VEGF_{121}$–$VEGF_{165}$ plasmid was transfected into HCT-15 cells. Cell migration was determined using the transfected HCT-15 cells. Cell migration ability of HCT-15 cells was enhanced in the presence of $VEGF_{165}$ (222 pM) but inhibited by the presence of $VEGF_{121}$–$VEGF_{165}$ plasmid. t-test, *$P<0.05$, $P<0.01$, *$p<0.001$, n=3.
Figure 6:
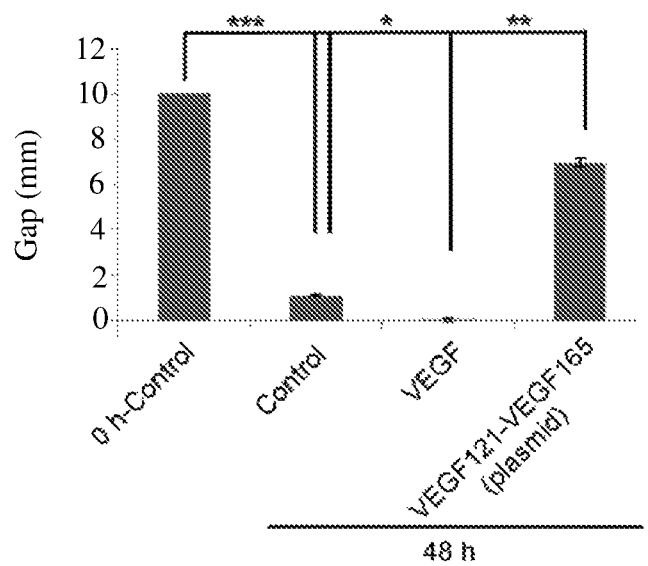

Cell migration is a critical process in angiogenesis and tumor metastasis. We examined whether cell migration was affected by the $VEGF_{121}$-$VEGF_{165}$ chimeric protein. Cell migration was examined by a gap-closure migration assay. Consistently, the $VEGF_{121}$-$VEGF_{165}$ protein significantly inhibited migration of 3B-11 cells in an autocrine manner See FIG. 5. In addition, the results showed that cell migration of HCT-15 induced by $VEGF_{165}$ was inhibited by the addition of the $VEGF_{121}$–$VEGF_{165}$ protein in a concentration-dependent manner. See FIG. 6, panel A. The $VEGF_{121}$–$VEGF_{165}$ protein significantly inhibited cell migration in a paracrine (FIG. 6, A) and an autocrine manner (FIG. 6, B). These data suggested that $VEGF_{121}$–$VEGF_{165}$ chimeric protein can inhibit migration of endothelial cells and tumor cells.

$VEGF_{121}$–$VEGF_{165}$ fusion protein impaired tumor invasion

Figure 7:
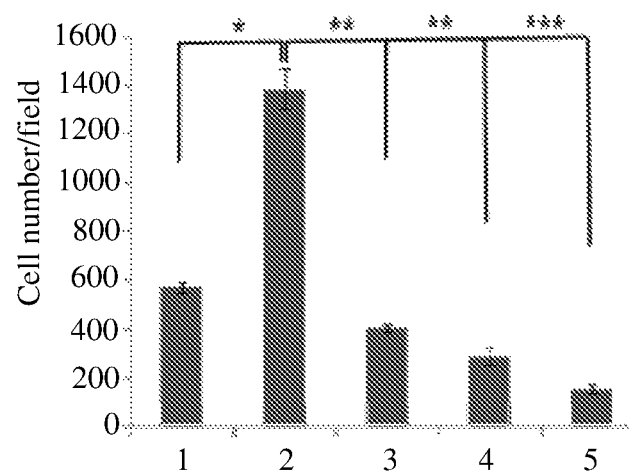
FIG. 7 is a graph showing the effect of the $VEGF_{121}$–$VEGF_{165}$ protein on cell invasion. HCT-15 cells were treated with different concentrations of VEGF $_{121}$–$VEGF_{165}$ (42, 83, 125 pM) in the presence of $VEGF_{165}$ (222 pM). Cell invasion was determined by the transwell chamber assay. After migrating for 48 h, the number of cells passing through the filter was counted after staining with crystal violet (original magnification: 400×). 1: Control; 2: $VEGF_{165}$; 3: $VEGF_{165}$+$VEGF_{121}$–$VEGF_{165}$ (42 pM); 4: $VEGF_{165}$+$VEGF_{121}$–$VEGF_{165}$ (83 pM); 5: $VEGF_{165}$+$VEGF_{121}$–$VEGF_{165}$ (125 pM). t-test, *$P<0.05$, $P<0.01$, * $p<0.001$.

To validate $VEGF_{121}$–$VEGF_{165}$ chimeric protein's effect on metastasis of tumor cells, we examined the effect of the protein on cell invasion by using the Transwell assay. In the absence of $VEGF_{121}$–$VEGF_{165}$, $VEGF_{165}$ induced invasive capability as indicated by intensive penetration. See FIG. 7. However, $VEGF_{165}$-induced cell invasion was inhibited by the addition of $VEGF_{121}$–$VEGF_{165}$ in a concentration-dependent manner in HCT-15 cancer cells. The number of penetrated cells was significantly decreased when treated with increased concentrations of the $VEGF_{121}$–$VEGF_{165}$ protein as compared with $VEGF_{165}$ only. See FIG. 7. These results indicated that the invasion of cancer cells was markedly suppressed by the addition of the $VEGF_{121}$–$VEGF_{165}$ protein, suggesting a role of the protein in suppressing cancer metastasis.

$VEGF_{121}$–$VEGF_{165}$ chimeric protein attenuated autocrine VEGFR2-HIF-1α-VEGF165/Lon signaling through PI3K-AKT-mTOR pathway To check whether $VEGF_{121}$–$VEGF_{165}$ attenuates HIF-1α signaling to decrease the resistance to anti-angiogenic therapy, we first examined the effect of $VEGF_{121}$–$VEGF_{165}$ on the VEGFR2-HIF-1α-$VEGF_{165}$ axis in tumor cells. Lon is upregulated by the hypoxia inducible factor-1α (HIF-1α) and involved in response to low oxygen availability, which adapt cancer cells to a hypoxic environment. We examined whether the fusion protein influenced the expression of Lon protease. The expression of HIF-1α, $VEGF_{165}$, and Lon was determined by Western blot analysis. The results showed that VEG1-R2-HIF-1α-$VEGF_{165}$/Lon signaling in HCT-15 cancer cells was activated by $VEGF_{165}$ treatment and hypoxia stimulated by cobalt chloride ($CoCl_2$) (data not shown). However, the signaling activation was inhibited by the addition of $VEGF_{121}$–$VEGF_{165}$ in a concentration-dependent manner under normoxia and hypoxia conditions. The recombinant $VEGF_{121}$–$VEGF_{165}$ protein reduced the level of HIF-1α, $VEGF_{165}$, Lon, and phospho-VEGFR2 induced by $VEGF_{165}$ and/or hypoxia (data not shown). Mechanically, the $VEGF_{121}$–$VEGF_{165}$ protein inhibited the activation of VEGFR2-HIF-1α-$VEGF_{165}$/Lon signaling through repressing PI3K-AKT-mTOR pathway (data not shown), suggesting that the $VEGF_{121}$–$VEGF_{165}$ protein overcame survival mechanism triggered by the PI3K-AKT-mTOR to VEGFR2-HIF-1α-$VEGF_{165}$/Lon axis under hypoxia. These data suggest that $VEGF_{121}$–$VEGF_{165}$ can inhibit autocrine VEGFR2-HIF-1α-$VEGF_{165}$/Lon signaling through PI3K-AKT-mTOR pathway in cancer cells.

$VEGF_{121}$–$VEGF_{165}$ fusion protein impaired tumor growth in vivo

Figure 8:
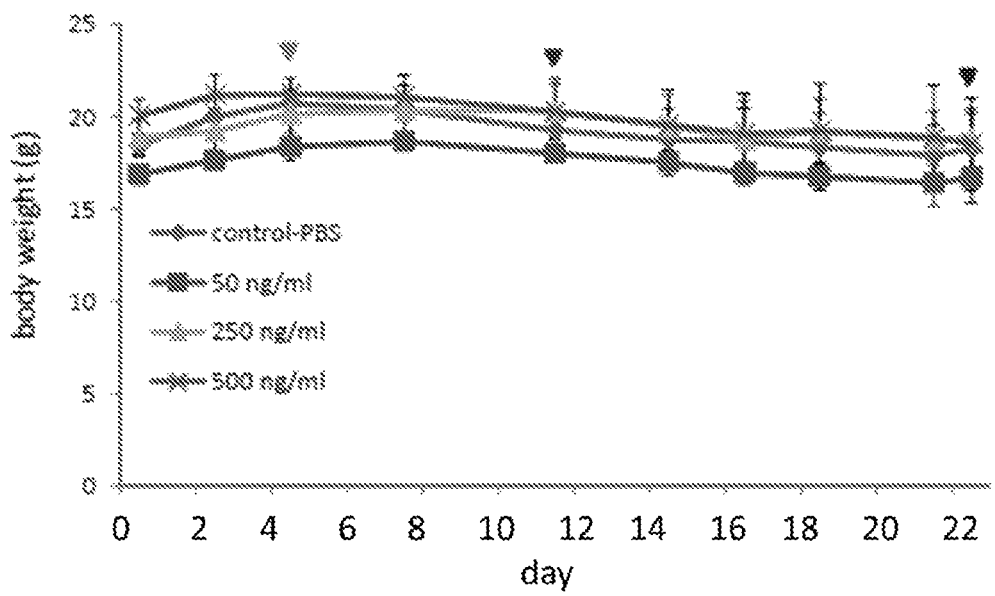
FIG. 8 is a set of graphs showing the effect of the $VEGF_{121}$–$VEGF_{165}$ protein in a xenograft tumorigenesis assay. HCT-15 cells were injected subcutaneously into the dorsal flank of nude mice (1 site per mouse). Injected mice were examined every two days for tumor formation. Different concentrations of $VEGF_{121}$–$VEGF_{165}$ protein (10, 50, or 250 ng/ml) or a PBS control were directly injected into the tumors in the mice. (A) The body weight of injected mice was monitored. (B) Tumor volume was estimated from its length and width, as measured by a 6-inch-dial caliper, using the formula: tumor volume=$l \times w^2 \times 0.52$.
Figure 8:
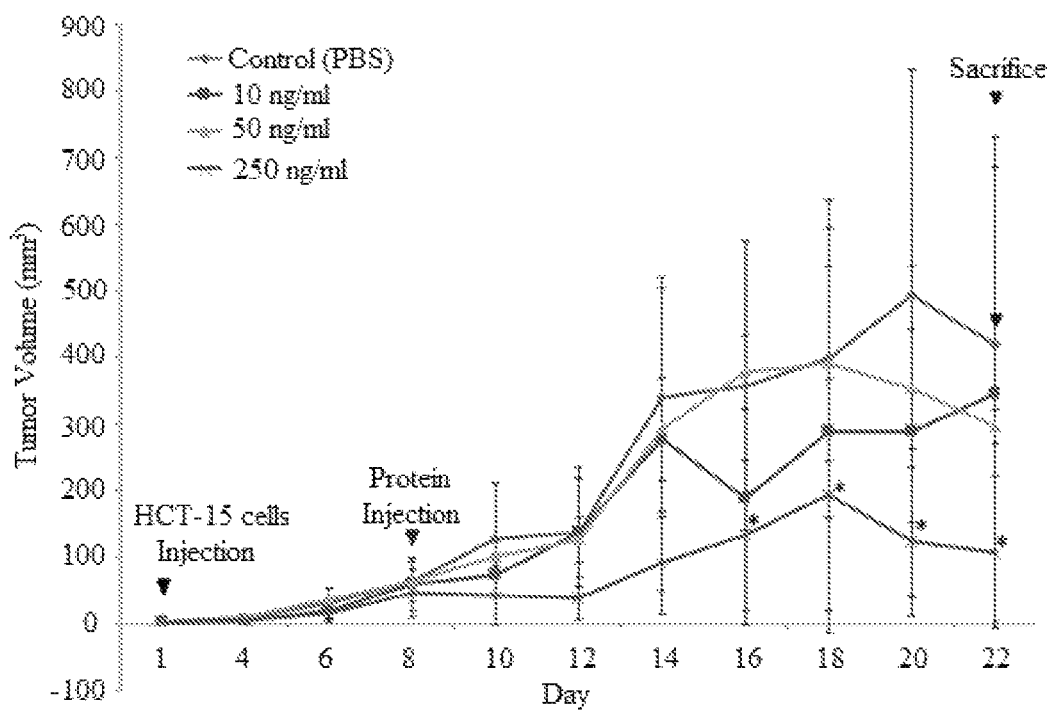

Our data demonstrated that the chimeric $VEGF_{121}$–$VEGF_{165}$ protein can arrest tube formation of endothelial cells and interfere with tumor cell growth, migration and invasion in vitro. A xenograft tumorigenesis assay was performed to demonstrate the inhibitory effect of the $VEGF_{121}$–$VEGF_{165}$ protein on tumors in vivo. BALB/c nude mice (6-8 weeks old) were used in the assay. $1 \times 10^6$ HCT-15 cells suspended in 0.2 ml of Matrigel were injected subcutaneously into the dorsal flank of nude mice (1 site per mouse). The mice were examined every two days for tumor formation. Different concentrations of the VEGF121–$VEGF_{165}$ protein (10, 50, or 250 ng/ml) or a PBS control were directly injected into the tumors in the mice. See FIG. 8, panel B. The body weight of the mice was monitored. See FIG. 8, panel A. The mice were then sacrificed by $CO_2$ euthanasia.

The body weight of the mice treated with the $VEGF_{121}$–$VEGF_{165}$ chimeric protein did not change significantly, suggesting that the protein was not toxic to the animals. See FIG. 8, panel A. The chimeric protein reduced tumor growth in the mice in a dose-dependent manner. See FIG. 8, panel B. Thus, the study demonstrated that the $VEGF_{121}$–$VEGF_{165}$ chimeric protein can suppress tumor growth in vivo.

Materials and Methods

Cell lines and cell cultures: 3B-11 cells were purchased from ATCC (#CRL-2160, Manassas, Va., USA). 3B-11 cells were maintained in DMEM and HCT-15 cells in RPMI-1640 supplemented medium with 10% (v/v) heat-inactivated FBS (fetal bovine serum qualified; Invitrogen), 1% PSA (penicillin-streptomycin amphotericin B; Biological industries, NY, USA) in a 37° C. humidified incubator with 5% $CO_2$.

Purification of $VEGF_{121}$–$VEGF_{165}$ recombinant proteins: The plasmids were transfected into 293T cells using the Biomics transfection reagent as described in the instruction manual of the pcDNA3.1 vector helper-free system (Biomics). After incubation for 36 hours, the supernatant of the 293T cell culture was collected and purified on Ni-NTA resin, eluted with 250 mmol/L imidazole according to the instruction manual. The recombinant protein was concentrated by the Microcon Centrifugal Filter Unit (Millipore, Bedford, Mass., USA). Finally, the purified protein was confirmed by 10% SDS-PAGE and Western Blotting.

Cell proliferation assay: The proliferation of 3B-11 cells and HCT-15 cells was assessed using CCK-8 dye reduction assay (Enzo, USA). 3B-11 or HCT-15 cells were pre-treated with different concentrations of $VEGF_{121}$–$VEGF_{165}$ (42, 83, 125 pM) for 30 min, a commercial $VEGF_{165}$ was added (222 pM, Abcam, Cambridge, Mass., USA), and then the cells were incubated for 24 hours. At the end of the treatment, 10 μl of the CCK-8 solution was added to each well of the plate and the plate was incubated for 2~4 hours in the incubator. After shaking the plate for 10 seconds, cell viability was assessed by measuring the absorbance at 450 nm using a microplate reader. All measurements were performed three times. The T-test was used to compare groups. Data are presented as mean±SD.

Colony formation assay: Clonogenic assay is an in vitro transformation assay based on the ability of a single cell to grow into a colony. To examine this, the plasmid of $VEGF_{121}$–$VEGF_{165}$ was transfected into HCT-15 in a 10 cm dish overnight and treated with $VEGF_{165}$ recombinant protein 222 pM as a positive control. Next day, the treated HCT-15 cells (~$1 \times 10^3$ per well) were plated in 6-well plates and incubated in a 37° C. incubator. Fresh RPMI medium containing 10% FBS was added every 48 hours. At the end of the 14th day, cells were washed twice with ice cold PBS, fixed with methanol for 10 minutes and then stained with 1% crystal violet in methanol for 15 minutes followed by washing with deionized water. Colonies with more than 50 cells were scored and counted under the microscope at 200×.

Cell migration assay: Cell migration assay was determined by gap closure assay. 3B-11 cells or HCT-15 cells were treated with different concentrations (42, 83, 125 pM) of the recombinant proteins for 16 h (37° C., 5% $CO_2$). These cells were trypsinized and resuspended in serum-free DMEM or RPMI-1640 medium. A total of $8 \times 10^5$ cells in 70

µl serum-free DMEM or RPMI-1640 were seeded in medium in each well (8×10⁵ cells/well) and incubated at 37° C., 5% $CO_2$ Next day, the ibidi culture-insert (Applied Biophysics, USA) was gently removed by using sterile tweezers, and each well was then filled with 2 ml 0.1% FBS medium. Cell migration was monitored for 48 h by microscope.

Tube formation assay: Corning Matrigel® Matrix (BD Biosciences, San Jose, Calif., USA) solution was thawed on ice overnight and 50 µl aliquots were coated onto a 96-well plate and incubated at 37° C. for 1 h to solidify. 50 µl of DMEM supplemented with 10% FBS medium containing about 8×10⁵ 3B-11 cells was seeded onto the plated Matrigel Matrix and incubated at 37° C. These cells were treated as previously described. The assay was done in triplicate and was incubated at 37° C. with 5% $CO_2$. Images of the formation of capillary-like structures were obtained after 2 h with a computer-assisted microscope (Olympus, Tokyo, Japan) at 200× magnification. Tubular structures were quantified by manually counting the numbers of connected cells in randomly selected fields at 200× magnification. Total tube numbers of network formation were counted.

Cell invasion assay: Cell invasion was evaluated using a transwell chamber (Corning Costar; Cambridge, Mass., USA) equipped with a Matrigel-coated filter membrane (8 µm pores). Briefly, the filters were pre-coated with 200 µg/ml basement membrane proteins (Matrigel; BD Biosciences, San Jose, Calif., USA) and allowed to dry overnight at 37° C. with 5% $CO_2$. HCT-15 cells (8×10⁵) in FBS-free medium were seeded in the upper chambers, and lower wells were filled with 10% FBS medium. After incubation at 37° C. for 48 h, non-migratory cells on the upper side of the insert were removed with a cotton swab. The cells that had passed through the filter were fixed in methanol and stained with crystal violet. Randomly selected fields on the lower side of the photograph under microscopy were counted.

Immunoblotting: HCT-15 cells were seeded onto a 10 mm dish at a density of 1.5×10⁶ cells in 10 ml medium for 24 h under normoxia and hypoxia ($CoCl_2$, Cobalt dichloride; 150 µM) and treated as previously described. Total protein concentrations were determined using a BCA protein assay. Equal quantities of total protein were resolved using 10% SDS-PAGE and electroblotted onto polyvinylidene fluoride membranes. Membranes were blocked with 5% skimmed milk and probed overnight at 4° C. with primary antibodies. Membranes were then probed with the appropriate HRP-conjugated secondary antibodies (GeneTex, Hsinchu, Taiwan) and the immunoreactive bands were visualized using an enhanced chemiluminescence method (Bio-Rad, Hercules, Calif., USA). Antibodies used in this study were purchased or produced as indicated. Antibody to human Lon was produced as described previously. See Wang et al., Cancer Sci 2010, 101(12):2612-2620; and Cheng et al., Cell death & disease 2013, 4, e681. Phospho-PI3K (Tyr458/Tyr199, #4228), phospho-AKT (Ser473, #4060), and phospho-mTOR (Ser2448, #2971) antibodies were obtained from Cell Signaling Technology (Beverly, Mass., USA); HIF-1α (#610958) antibodies was obtained from BD Biosciences (Franklin Lakes, N.J.); phospho-VEGFR2 (Tyr1054/Tyr1059, ab5473), VEGF-165A (ab69479) antibodies were from Abcam (Cambridge, Mass., USA); beta-actin antibody was fromfrom GeneTex (GTX109639, Hsinchu, Taiwan).

Statistical methods: Parametric Student's t test was used in this study to judge the significance of difference between conditions of interest. In general, a P value of <0.05 was considered as statistically significant (Student's t test, $*p<0.05$, $p<0.01$, and $*p<0.001$).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

---

What is claimed is:

1. A fusion protein, comprising:
   (i) a first vascular endothelial growth factor (VEGF) isoform, and
   (ii) a second VEGF isoform, and
   (iii) a dimerization domain between the first isoform and the second isoform, wherein the dimerization domain contains two Fc regions, and wherein the first isoform and the second isoform are selected from $VEGF_{121}$ and $VEGF_{165}$.

2. The fusion protein of claim 1, further comprising a linker between the two Fc regions.

3. The fusion protein of claim 2, wherein the fusion protein contains, in the direction from the N-terminus to the C-terminus, $VEGF_{121}$, one of the two Fc regions, the linker, the other of the two Fc regions, and $VEGF_{165}$.

4. The fusion protein of claim 2, wherein the fusion protein contains, in the direction from the N-terminus to the C-terminus, $VEGF_{165}$, one of the two Fc regions, the linker, the other of the two Fc regions, and $VEGF_{121}$.

5. The fusion protein of claim 2, wherein the linker is a flexible linker consisting of 15 to 30 amino acids.

6. The fusion protein of claim 5, wherein the linker is (Gly-Gly-Gly-Gly-Ser)$_n$, wherein n is 3.

7. The fusion protein of claim 6, wherein each of the Fc regions is a human IgG1 Fc region.

8. The fusion protein of claim 7, further comprising a peptide tag.

9. The fusion protein of claim 8, wherein the tag is a C-terminal 6X-His tag.

10. The fusion protein of claim 9, further comprising an N-terminal signal peptide.

11. The fusion protein of claim 10, wherein the fusion protein has the sequence of SEQ ID NO: 11.

12. A pharmaceutical composition, comprising the fusion protein of claim 1 and a pharmaceutically acceptable carrier.

* * * * *